(12) United States Patent
Wolek et al.

(10) Patent No.: US 7,776,093 B2
(45) Date of Patent: Aug. 17, 2010

(54) VERTEBRAL BODY REPLACEMENT APPARATUS AND METHOD

(75) Inventors: Howard Wolek, Morris Plaine, NJ (US);
Franceso Larosa, Neptune, NJ (US);
Jeffrey A. Kozak, Houston, TX (US);
Mark A. Lorenz, Hinsdale, IL (US);
Michael R. Zindrick, Hinsdale, IL (US)

(73) Assignee: Blackstone Medical, Inc., Charlotte, NC (US)

( * ) Notice: Subject to any disclaimer, the term of this patent is extended or adjusted under 35 U.S.C. 154(b) by 858 days.

(21) Appl. No.: 10/968,586

(22) Filed: Oct. 19, 2004

(65) Prior Publication Data

US 2005/0154459 A1 Jul. 14, 2005

Related U.S. Application Data

(60) Provisional application No. 60/512,716, filed on Oct. 20, 2003.

(51) Int. Cl.
*A61F 2/44* (2006.01)
(52) U.S. Cl. .................................................. 623/17.16
(58) Field of Classification Search .... 623/17.11–17.16
See application file for complete search history.

(56) References Cited

U.S. PATENT DOCUMENTS

| | | | |
|---|---|---|---|
| 4,759,769 A | | 7/1988 | Hedman et al. |
| 4,892,545 A | | 1/1990 | Day et al. |
| 5,192,327 A | | 3/1993 | Brantigan |
| 5,360,430 A | | 11/1994 | Lin |
| 5,397,364 A | | 3/1995 | Kozak et al. |
| 5,458,641 A | * | 10/1995 | Ramirez Jimenez ..... 623/17.11 |
| 5,916,267 A | | 6/1999 | Tienboon |
| 6,039,761 A | | 3/2000 | Li et al. |
| 6,045,579 A | | 4/2000 | Hochshuler et al. |
| 6,086,613 A | * | 7/2000 | Camino et al. ........... 623/17.16 |
| 6,126,689 A | * | 10/2000 | Brett ........................ 623/17.16 |
| 6,159,211 A | | 12/2000 | Boriani et al. |
| 6,241,769 B1 | | 6/2001 | Nicholson et al. |
| 6,395,030 B1 | | 5/2002 | Songer et al. |
| 6,409,766 B1 | | 6/2002 | Brett |
| 6,432,107 B1 | | 8/2002 | Ferree |
| 6,447,544 B1 | | 9/2002 | Michelson |

(Continued)

FOREIGN PATENT DOCUMENTS

WO  WO 00/13619  3/2000

(Continued)

OTHER PUBLICATIONS

International Search Report, Jan. 31, 2006.

*Primary Examiner*—Alvin J Stewart
(74) *Attorney, Agent, or Firm*—Baker & McKenzie LLP

(57) ABSTRACT

Various embodiments of the present invention relate to an apparatus for vertebral body replacement and methods associated therewith. In one embodiment, a vertebral body replacement apparatus may be used to correct and stabilize the spine (e.g., the thoracolumbar spine (T1-L5)). In another embodiment, a vertebral body (e.g., a diseased and/or damaged vertebral body) that has been resected or excised (e.g., for the treatment of a tumor or trauma) may be replaced (with the height of the resected or excised vertebral body being substantially replaced and restored by the apparatus of the present invention).

22 Claims, 21 Drawing Sheets

U.S. PATENT DOCUMENTS

| | | | |
|---|---|---|---|
| 6,468,311 B2 | 10/2002 | Boyd et al. | |
| 6,475,219 B1 | 11/2002 | Shelokov | |
| 6,500,205 B1 | 12/2002 | Michelson | |
| 6,562,074 B2 | 5/2003 | Gerbec et al. | |
| 6,579,290 B1 | 6/2003 | Hardcastle et al. | |
| 6,610,093 B1 | 8/2003 | Pisharodi | |
| 6,613,051 B1 | 9/2003 | Luk et al. | |
| 6,660,038 B2 * | 12/2003 | Boyer et al. | 623/17.15 |
| 6,682,561 B2 * | 1/2004 | Songer et al. | 623/17.11 |
| 6,723,126 B1 | 4/2004 | Berry | |
| 6,749,635 B1 * | 6/2004 | Bryan | 623/17.16 |
| 6,758,862 B2 * | 7/2004 | Berry et al. | 623/17.16 |
| 6,808,538 B2 * | 10/2004 | Paponneau | 623/17.16 |
| 6,852,129 B2 | 2/2005 | Gerbec et al. | |
| 6,893,464 B2 * | 5/2005 | Kiester | 623/17.11 |
| 6,960,232 B2 * | 11/2005 | Lyons et al. | 623/17.16 |
| 7,018,415 B1 * | 3/2006 | McKay | 623/17.15 |
| 7,147,665 B1 * | 12/2006 | Bryan et al. | 623/17.16 |
| 2002/0052656 A1 | 5/2002 | Michelson | |
| 2002/0077702 A1 | 6/2002 | Castro | |
| 2002/0091446 A1 | 7/2002 | Zucherman et al. | |
| 2002/0128652 A1 | 9/2002 | Ferree | |
| 2002/0128715 A1 | 9/2002 | Bryan et al. | |
| 2002/0169508 A1 | 11/2002 | Songer et al. | |
| 2003/0023312 A1 | 1/2003 | Thalgott | |
| 2003/0040799 A1 | 2/2003 | Boyd et al. | |
| 2003/0045940 A1 | 3/2003 | Eberlein et al. | |
| 2003/0100950 A1 | 5/2003 | Moret | |
| 2003/0125739 A1 | 7/2003 | Bagga et al. | |
| 2003/0171813 A1 | 9/2003 | Kiester | |
| 2003/0187506 A1 * | 10/2003 | Ross et al. | 623/17.13 |
| 2004/0030387 A1 | 2/2004 | Landry et al. | |
| 2004/0068318 A1 | 4/2004 | Coates et al. | |
| 2004/0073314 A1 | 4/2004 | White et al. | |
| 2005/0060034 A1 | 3/2005 | Berry et al. | |
| 2005/0060036 A1 | 3/2005 | Schultz et al. | |
| 2006/0058877 A1 | 3/2006 | Gutlin et al. | |

FOREIGN PATENT DOCUMENTS

WO     WO 02/96474 A1     12/2002

* cited by examiner

VERTEBRAL BODY REPLACEMENT APPARATUS AND METHOD

CROSS-REFERENCE TO RELATED APPLICATIONS

This application claims the benefit under 35 U.S.C. 119(e) of U.S. Provisional Application Ser. No. 60/512,716, filed Oct. 20, 2003.

FIELD OF THE INVENTION

Various embodiments of the present invention relate to an apparatus for vertebral body replacement and methods associated therewith.

In one embodiment, a vertebral body replacement apparatus may be used to correct and stabilize the spine (e.g., the thoracolumbar spine (T1-L5)).

In another embodiment, a vertebral body (e.g., a diseased and/or damaged vertebral body) that has been resected or excised (e.g., for the treatment of a tumor or trauma) may be replaced (with the height of the resected or excised vertebral body being substantially replaced and restored by the apparatus of the present invention).

BACKGROUND OF THE INVENTION

Examples of various patent documents in the spinal implant area include the following:

U.S. Pat. No. 5,192,327 to Brantigan relates to a surgical prosthetic implant for vertebrae. More particularly, surgical prosthetic modular implants used singularly or stacked together are provided to support and fuse together adjacent vertebrae or to totally or partially replace one or more vertebrae in a vertebral column. The implants are rigid annular plugs, dimensionally similar to normal vertebral bodies, have simplified oval or hemi-oval shapes with ridged faces to engage adjacent vertebral bodies to resist displacement and allow bone ingrowth and fusion and to interdigitate with the ridges of an adjacent plug for modular stacking to allow variability of ultimate implant height. The implants can be provided in sets of different thicknesses and are internally grooved to receive an upstanding connecting bar to bind together the individual stacked implants into a stable unit. The annular implants have ample spaces to allow ingrowth of blood capillaries and packing of bone graft and are preferably made of a radiolucent material, preferably biocompatible carbon fiber reinforced polymers or are alternately made of traditional orthopaedic implant materials such as nickel, chromium, cobalt, stainless steel or titanium.

U.S. Pat. No. 5,397,364 to Kozak et al. relates to an anterior interbody fusion device. More particularly, an interbody fusion device includes a pair of lateral spacers and a pair of central spacers, each sized for percutaneous introduction through a disc resection portal in the disc annulus. Each of the lateral spacers includes opposing side faces defining a channel therein, while each of the central spacers includes arms at their opposite ends configured to be received within a channel of a corresponding lateral spacer. The arms and channels are interlocking to prevent separation of the components once assembled within the intradiscal space. The assembly of the central and lateral spacers defines a cavity therebetween for insertion of bone graft material. The central and lateral spacers are configured so that the bone graft cavity is oriented over the weakest, but most vascular and biologically active, bone of the vertebral body, while the lateral spacers are situated adjacent the disc annulus and over the strongest vertebral bone.

U.S. Pat. No. 6,159,211 to Boriani et al. relates to a stackable cage system for corpectomy/vertebrectomy. More particularly, surgical prosthetic modular devices used singularly or stacked together are provided for use to replace excised vertebral tissue. The devices are rigid plugs, dimensionally similar to normal vertebral bodies, and have ridged faces to engage adjacent vertebral bodies or to interdigitate when stacked. Ridges extend in both the medial/lateral and anterior/posterior directions to prevent slipping in the anterior/posterior and medial/lateral directions respectively. A locking screw may be used to secure a stack to form a singular rigid prosthetic device. The devices are also provided with a plurality of threaded openings. In the method of this invention, a device is used to replace excised vertebral tissue, threaded bolts are inserted into the threaded openings, and other spine stabilization devices are attached to the bolts. In corporectomies, the device can be bolted to a plate, which in turn is fixed to adjacent vertebrae. In spondylectomies, the device can be fixed to a series of posteriorly placed rods.

U.S. Pat. No. 6,468,311 to Boyd et al. relates to a modular interbody fusion implant. More particularly, an interbody fusion device for engagement between vertebrae includes a pair of lateral spacers for spacing the vertebrae, and a connecting member adapted to couple together the lateral spacers when inserted between the vertebrae. The connecting member, individual lateral spacers, or the entire spinal spacer can be made of bone in order to promote fusion of the vertebrae. The modular construction permits use of bone segments otherwise unsuitable due to size or strength in stable fusion devices.

U.S. Patent Application No. 2003/0040799 in the name of Boyd et al. relates to a modular interbody fusion implant. More particularly, an interbody fusion device for engagement between vertebrae includes a pair of lateral spacers for spacing the vertebrae, and a connecting member adapted to couple together the lateral spacers when inserted between the vertebrae. The connecting member, individual lateral spacers, or the entire spinal spacer can be made of bone in order to promote fusion of the vertebrae. The modular construction permits use of bone segments otherwise unsuitable due to size or strength in stable fusion devices.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
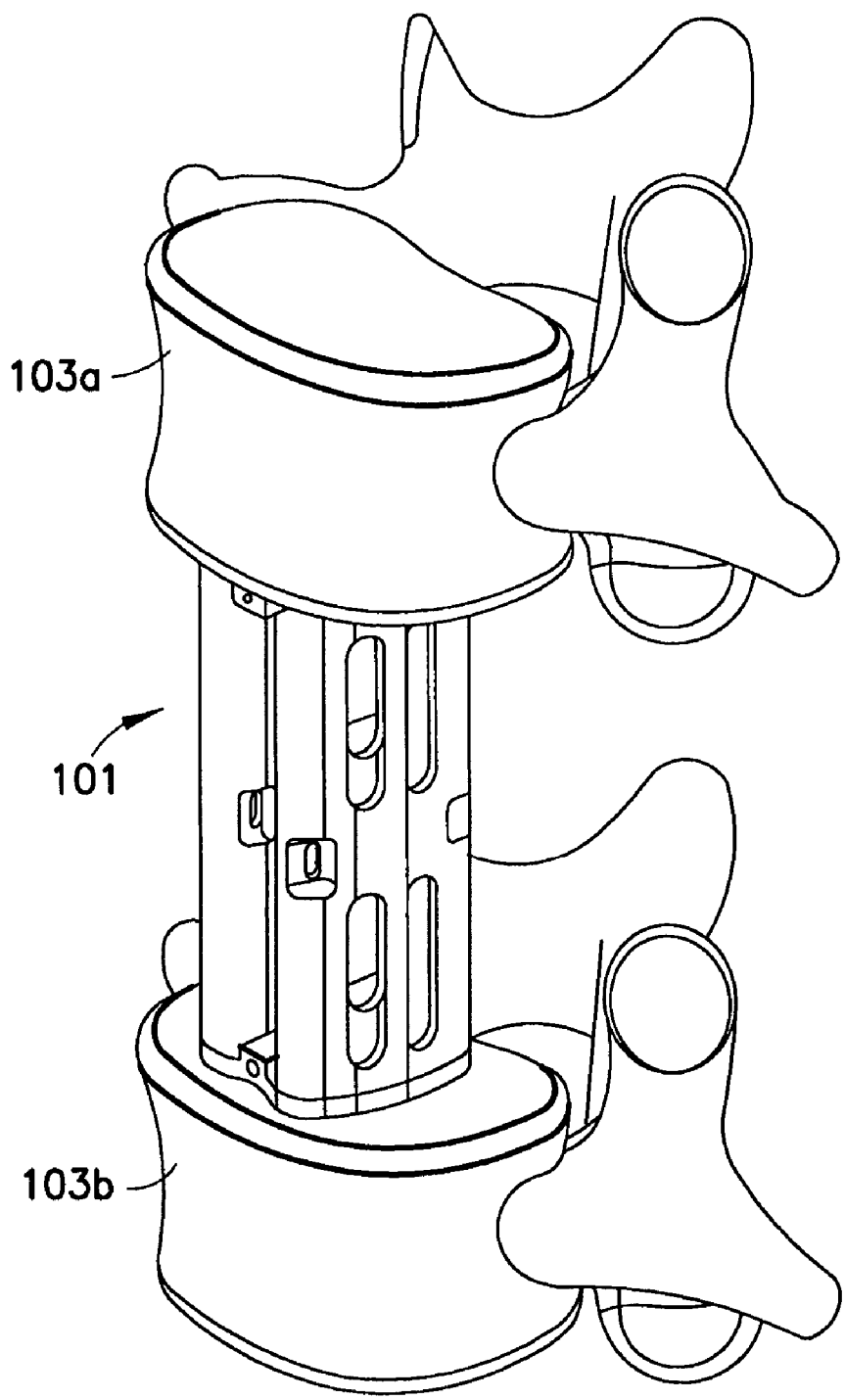
FIG. 1 shows a perspective view of one embodiment of a vertebral body replacement implant assembly according to the present invention.
Figure 2:
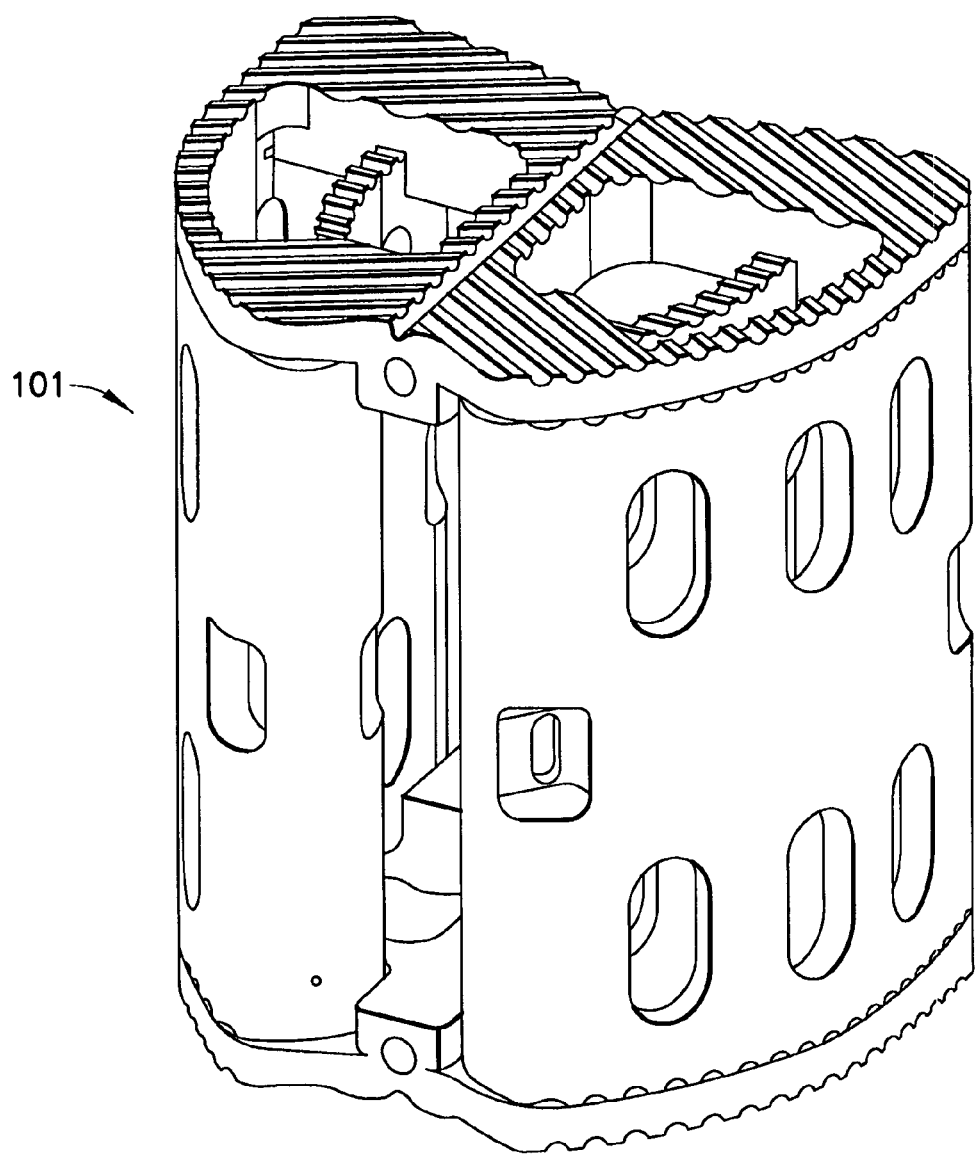
FIG. 2 shows another view of the implant assembly of FIG. 1 as it would look outside of the body.

Referring now to FIG. 1, one embodiment of a vertebral body replacement implant assembly according to the present invention is shown. As seen in this FIG. 1, Implant Assembly 101 may be implanted between First Vertebra 103a and Second Vertebra 103b (FIG. 2 shows another view of Implant Assembly 101 as it would look outside of the body). Of note, Implant Assembly 101 may be formed of a number of components fitted together.

Figure 3A:
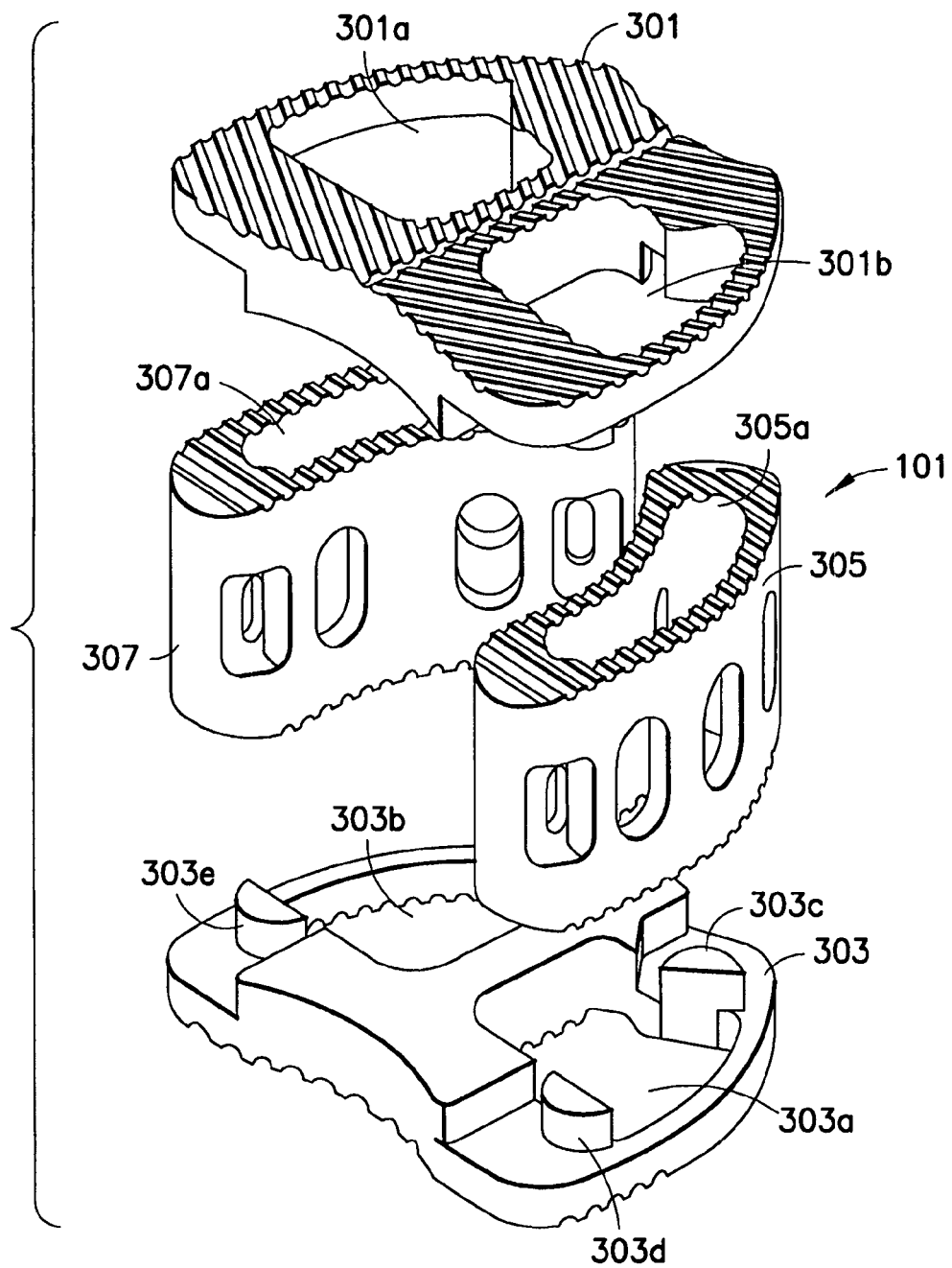
FIGS. 3A and 3B show exploded perspective views of the implant assembly of FIGS. 1 and 2 (FIG. 3A shows an embodiment of the implant assembly from one angle and FIG. 3B shows an embodiment of the implant assembly from another angle)
Figure 3B:
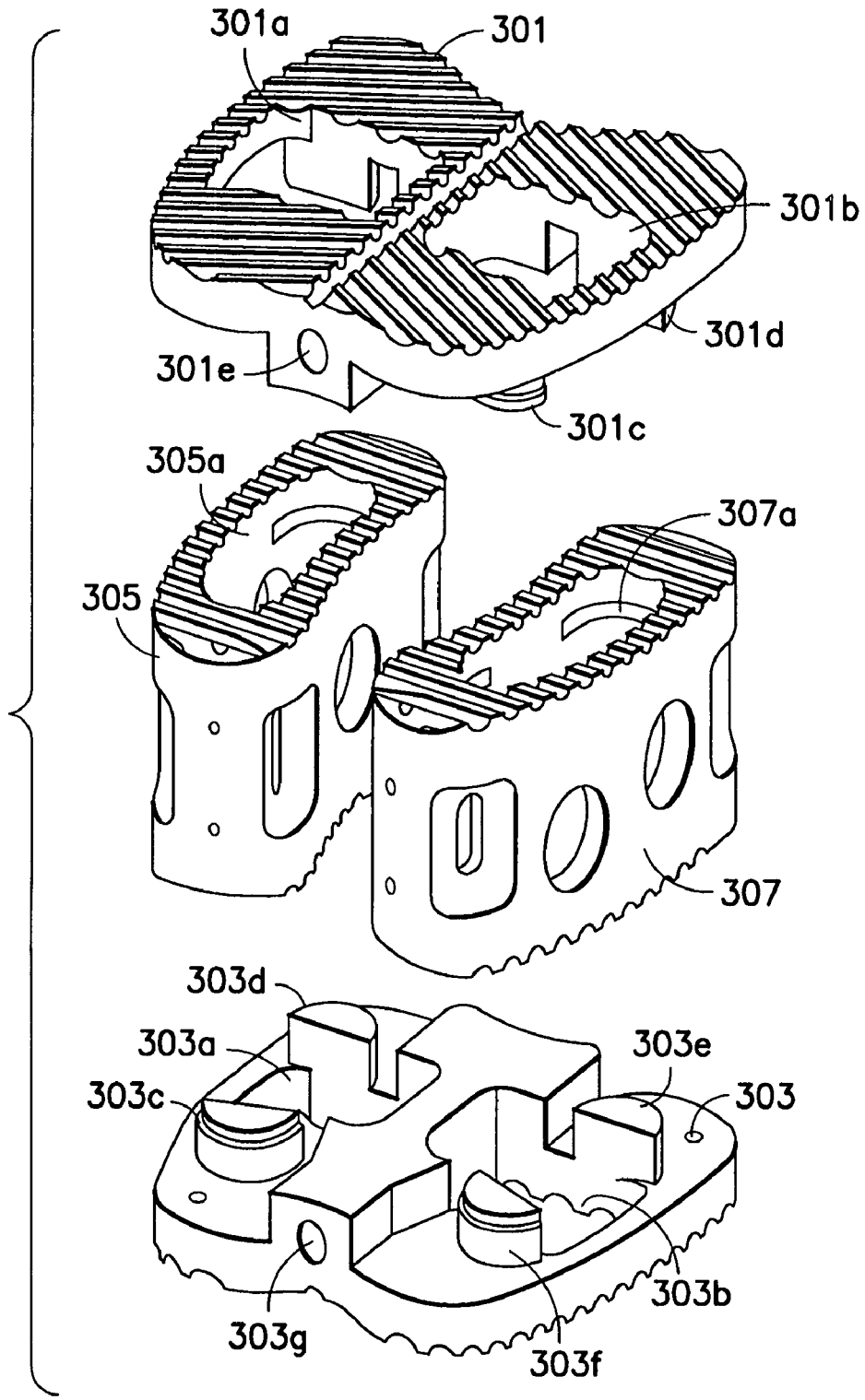

More particularly, as seen in FIGS. 3A and 3B, Implant Assembly 101 may be formed of, for example, four components: (a) First Endplate 301 (e.g., a top Endplate), Second Endplate 303 (e.g., a bottom Endplate), First Lateral Spacer 305 and Second Lateral Spacer 307.

First Endplate 301 may include: First Offset Aperture 301a (e.g., offset relative to a centerline of Endplate 301); Second Offset Aperture 301b (e.g., offset relative to a centerline of Endplate 301); Protrusions 301c and 301d (these Protrusions are seen most clearly in FIG. 3B; although in this embodiment there are four such Protrusions (two adjacent First Offset Aperture 301a and two adjacent Second Offset Aperture 301b) any number of protrusions may be utilized); Insertion Tool Mating Aperture 301e (for mating with an insertion tool (not shown)); and various grooves disposed along the top surface (the grooves are not separately numbered in the Figs.).

Likewise, Second Endplate 303 may include: First Offset Aperture 303a (e.g., offset relative to a centerline of Endplate 303); Second Offset Aperture 303b (e.g., offset relative to a centerline of Endplate 303); Protrusions 303c-303f; Insertion Tool Mating Aperture 303g (for mating with an insertion tool (not shown)); and various grooves disposed along the bottom surface (the grooves are not separately numbered in the Figs.).

Further, First Lateral Spacer 305 may include: Main Aperture 305a (which may at least partially line-up with First Offset Aperture 301a and First Offset Aperture 303a; various Auxiliary Apertures (not separately numbered in the Figs.); and various grooves disposed along the top surface and the bottom surface (the grooves are not separately numbered in the Figs.).

Likewise, Second Lateral Spacer 307 may include: Main Aperture 307a (which may at least partially line-up with Second Offset Aperture 301b and Second Offset Aperture 303b; various Auxiliary Apertures (not separately numbered in the Figs.); and various grooves disposed along the top surface and the bottom surface (the grooves are not separately numbered in the Figs.).

Of note, the embodiments of FIGS. 3A and 3B are similar, with the main differences being the shape of the internal centerline bosses on the inner faces of the First Endplate and Second Endplate and the fact that the Protrusions in the embodiment of FIG. 3A are essentially featureless (such that they provide lateral alignment/support) while the Protrusions of the embodiment of FIG. 3B provide locking features such as the ridges shown in the Fig. but not separately numbered (such that the ridges cooperate with mating indentations (shown in the Fig. but not separately numbered) in the First Lateral Spacer and the Second Lateral Spacer to provide both lateral alignment/support as well as up-down locking (e.g., removable locking) of the components). In another example (which example is intended to be illustrative and not restrictive), a tab and slot system may be utilized for locking.

Of further note, Implant Assembly 101 may provide for bony ingrowth and/or may be packed with bone matter. This may be accomplished via the hollow fenestrated design of the components (e.g., via First Offset Aperture 301a; Second Offset Aperture 301b; First Offset Aperture 303a; Second Offset Aperture 303b; Main Aperture 305a; Main Aperture 307a; and/or the various Auxiliary Apertures) and/or the hollow fenestrated design of the finished implant assembly (e.g., via the space(s) between First Lateral Spacer 305 and Second Lateral Spacer 307 at each end of the finished implant assembly).

In one set of examples (which examples are intended to be illustrative and not restrictive), Implant Assembly 101 may be provided in two footprint sizes. The "small" footprint may measure, for example, 28 mm wide×23 mm length (in this example each "small" footprint size Endplate may be 28 mm wide×23 mm length, and each Lateral Spacer may be 8 mm wide×23 mm length). The "large" footprint may measure, for example, 35 mm wide×28 mm length (in this example each "large" footprint size Endplate may be 35 mm wide×28 mm length, and each Lateral Spacer may be 8 mm wide×28 mm length). One or both footprint sizes may be available in height ranges from, for example, 12 mm to 60 mm (in increments of one millimeter, for example).

Figure 4:
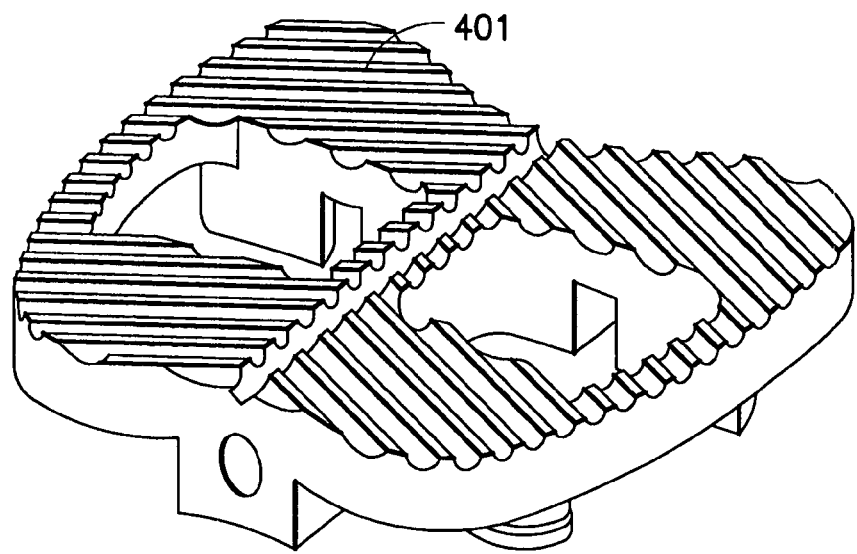
FIG. 4 shows a perspective view of an endplate type component of an implant assembly according to an embodiment of the present invention.
Figure 5:
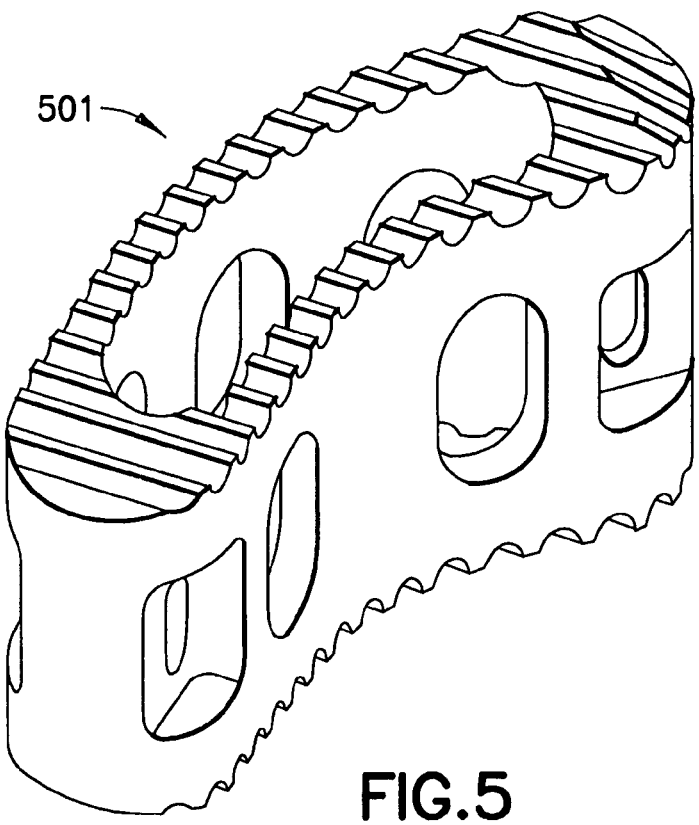
FIG. 5 shows a perspective view of a non-lordotic lateral spacer type component of an implant assembly according to an embodiment of the present invention.
Figure 6:
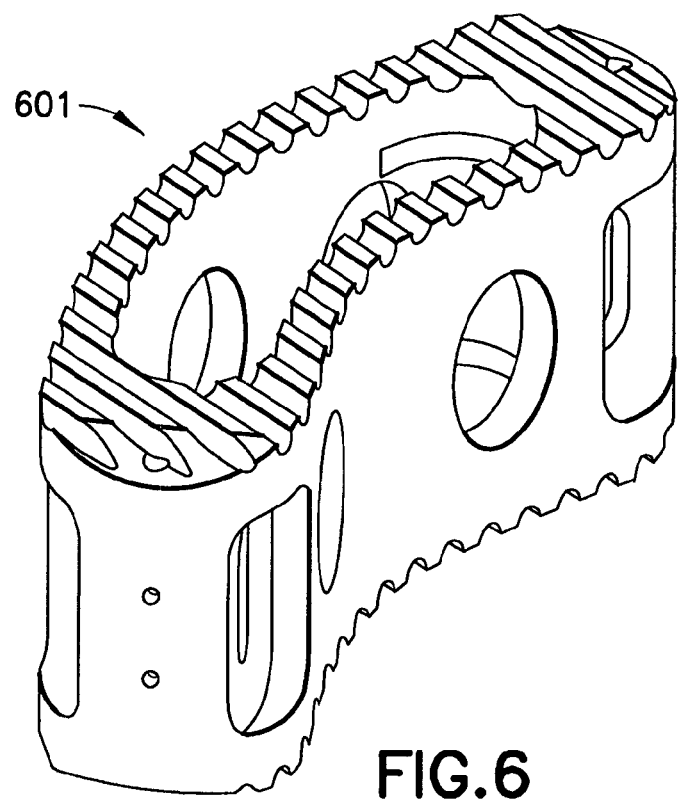
FIG. 6 shows a perspective view of a lordotic lateral spacer type component of an implant assembly according to an embodiment of the present invention.

Reference will now be made to Tables 1-3, below, which identify example thicknesses of the components of a "large" implant assembly (of course, these examples are intended to be illustrative and not restrictive). More particularly, Table 1 identifies example thicknesses of a "large" End Plate (see, e.g., FIG. 4 for a perspective view of this type of component), Table 2 identifies example thicknesses of a "large" Non-Lordotic Lateral Spacer (see, e.g., FIG. 5 for a perspective view of this type of component) and Table 3 identifies example thicknesses of a "large" Lordotic Lateral Spacer (see, e.g., FIG. 6 for a perspective view of this type of component).

TABLE 1

(All measurements in mm)

| 2 | 3 | 4 |
|---|---|---|

TABLE 2

(All measurements in mm)

| 8 | 10 | 12 | 14 | 16 | 21 | 26 | 31 | 36 | 41 | 46 | 51 | 56 |
|---|----|----|----|----|----|----|----|----|----|----|----|----|

TABLE 3

(All measurements in mm)

| 8 | 10 | 12 | 14 | 16 | 21 | 26 | 31 | 36 | 41 | 46 | 51 | 56 |
|---|----|----|----|----|----|----|----|----|----|----|----|----|

Reference will now be made to Tables 4-6, below, which identify example thicknesses of the components of a "small" implant assembly (of course, these examples are intended to be illustrative and not restrictive). More particularly, Table 4 identifies example thicknesses of a "small" End Plate (see, e.g., FIG. 4 for a perspective view of this type of component), Table 5 identifies example thicknesses of a "small" Non-Lordotic Lateral Spacer (see, e.g., FIG. 5 for a perspective view of this type of component) and Table 6 identifies example thicknesses of a "small" Lordotic Lateral Spacer (see, e.g., FIG. 6 for a perspective view of this type of component).

TABLE 4

(All measurements in mm)

| 2 | 3 | 4 |
|---|---|---|

TABLE 5

(All measurements in mm)

| 8 | 10 | 12 | 14 | 16 | 21 | 26 | 31 | 36 | 41 | 46 | 51 | 56 |
|---|----|----|----|----|----|----|----|----|----|----|----|----|

TABLE 6

(All measurements in mm)

| 8 | 10 | 12 | 14 | 16 | 21 | 26 | 31 | 36 | 41 | 46 | 51 | 56 |
|---|----|----|----|----|----|----|----|----|----|----|----|----|

Figure 7:
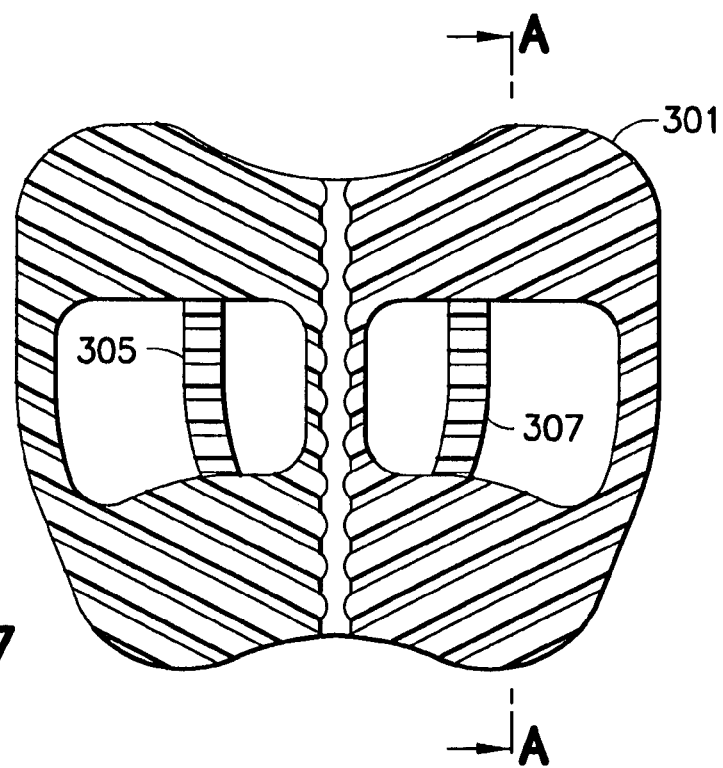
FIG. 7 shows a plan view of an implant assembly according to an embodiment of the present invention.
Figure 8:
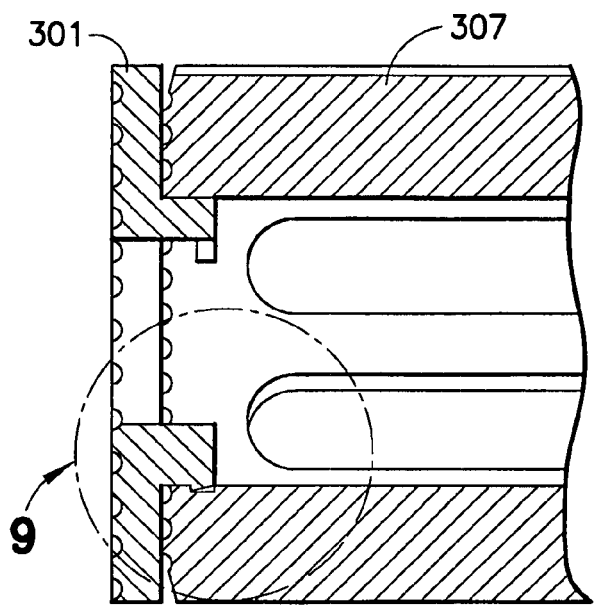
FIG. 8 shows section A-A of FIG. 7.
Figure 9:
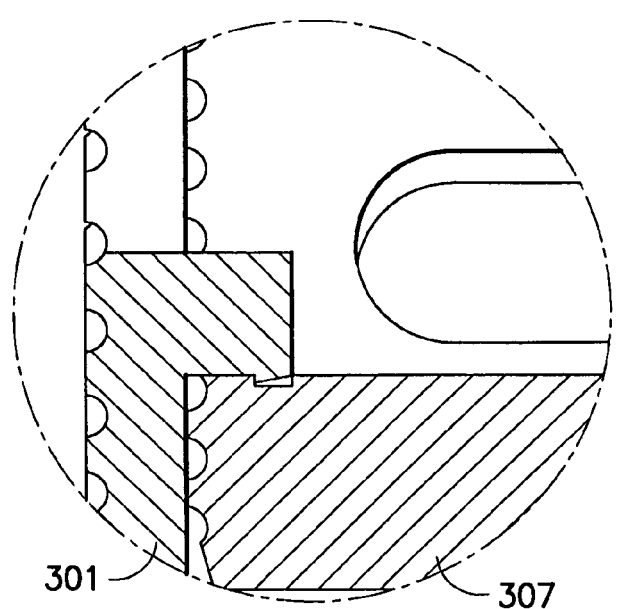
FIG. 9 shows Detail B of FIG. 8.
Figure 10:
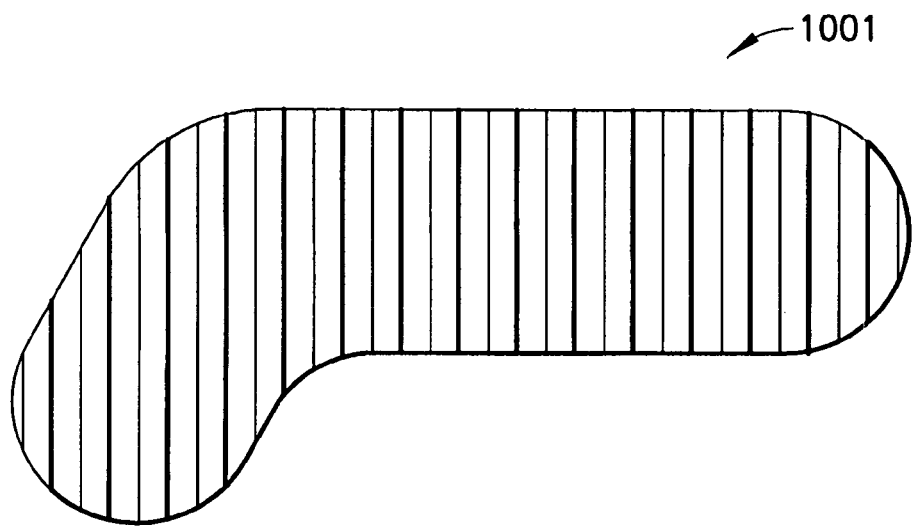
FIG. 10 shows a plan view of another embodiment of the present invention.
Figure 11:
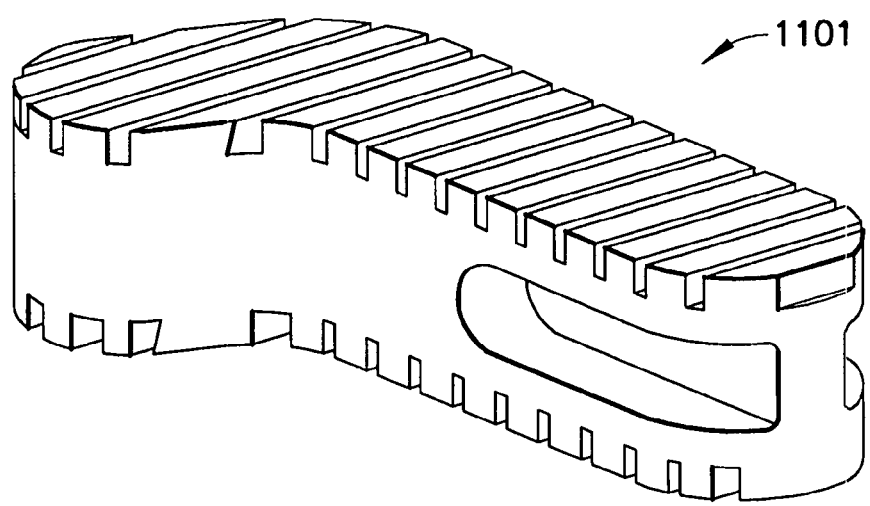
FIGS. 11-14 show perspective views of other embodiments of the present invention.
Figure 12:
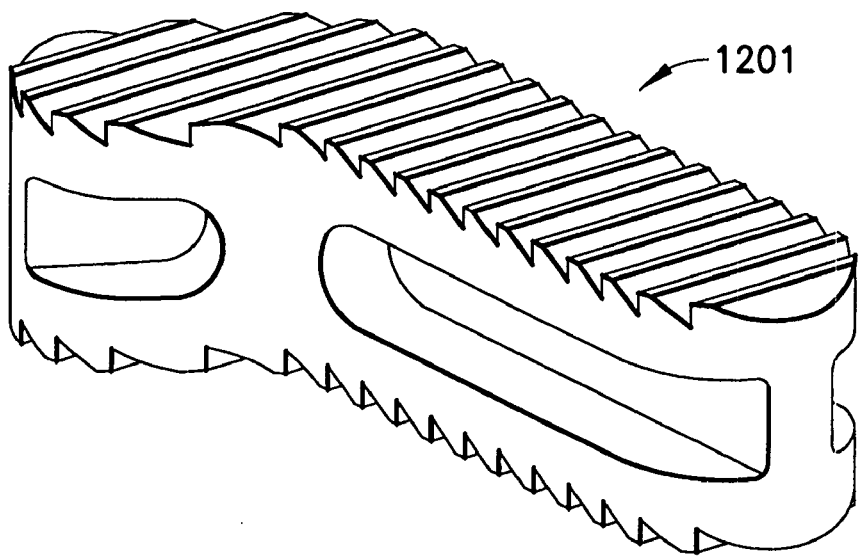
Figure 13:
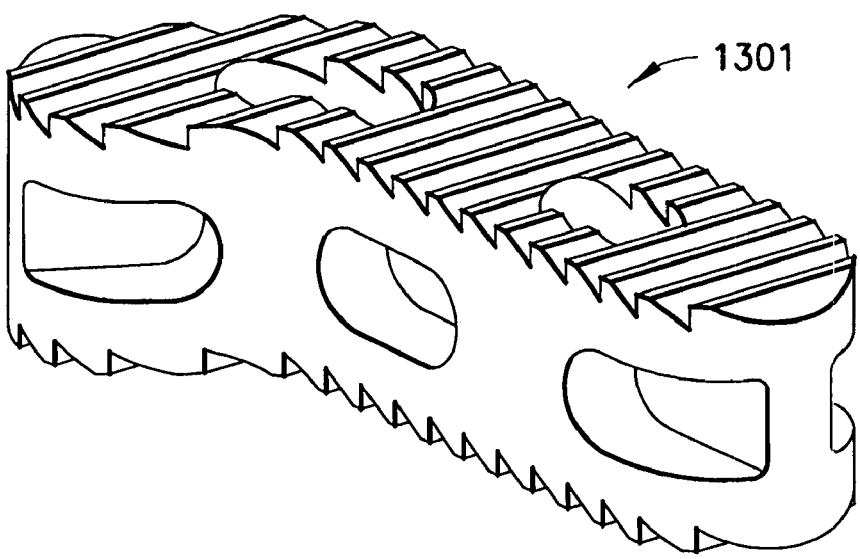
Figure 14:
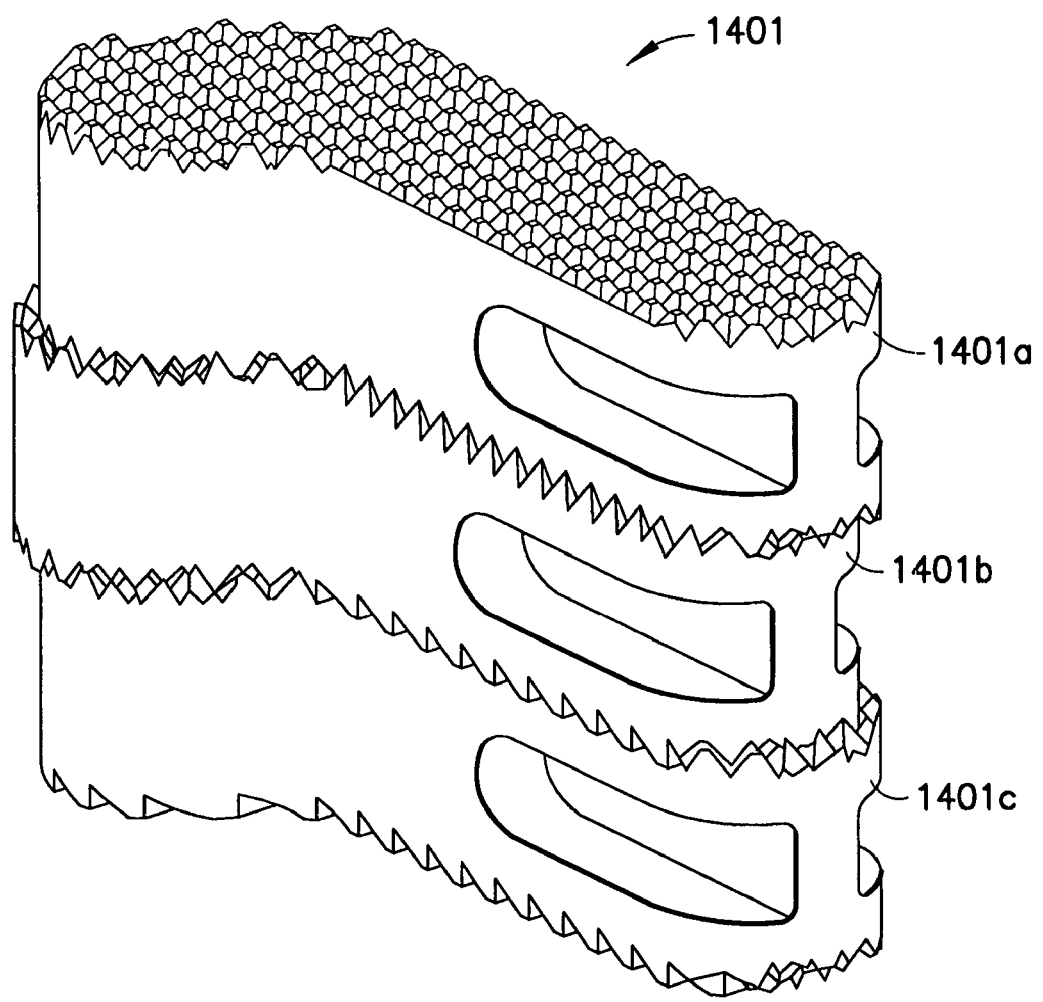

Referring now to construction of the implant assembly from its constituent components, it is noted that in one embodiment such construction may occur outside of the patient's body (e.g., outside of the wound). More particularly, after determining the correct height, footprint and/or lordotic requirement of the implant assembly, the surgeon may then select one or more lateral spacers (e.g., two) and/or one or more endplates (e.g., two) that would meet the requirements (e.g., a 30 mm tall implant assembly may utilize two lateral spacers of 26 mm tall and two 2 mm thick endplates). The components may be assembled by snapping the lateral spacers onto a first endplate and then snapping a second endplate onto the two lateral spacers. Such snapping construction may be carried out, for example, using a lip and undercut arrangement (see FIG. 7 (showing a plan view of an implant assembly according to an embodiment of the present invention), FIG. 8 (showing section A-A of FIG. 7), and FIG. 9 (showing Detail B of FIG. 8)). More particularly, with regard to such snapping construction, attention is directed to the features of FIG. 9 which show the undercut in the lateral spacer and the tapered lip on the endplate (wherein an interference may exist in the assembly until the tapered lip reaches the undercut and snaps into place creating a lock).

In another embodiment, some or all of the components may include or be made essentially entirely from polyetheretherketone (e.g., PEEK Optima). Of note, this PEEK polymer material has radiolucent properties, which may aid the surgeon in determining if fusion (e.g., in the operative site) has occurred. Since such PEEK material is essentially transparent to x-rays, markers (e.g., markers made of titanium) may be inserted into one or more of the components to give a surgeon a visual aid in determining the location of the component and/or entire implant assembly (e.g., both inter and postoperatively).

In another embodiment, Indications relating to use of the present invention may include (but not be limited to):
 For use in thoracolumbar spine (i.e., T1 to L5) to replace a vertebral body (e.g., a diseased vertebral body) resected or excised (e.g., for the treatment of tumor(s)) to achieve anterior decompression of the spinal cord and neural tissues, and to restore the height of a collapsed vertebral body.
 For treating fracture(s) of the thoracic and/or lumbar spine.
 To restore the biomechanical integrity of the anterior, middle, and/or posterior spinal column (e.g., even in the absence of fusion for a prolonged period).
 For use with supplemental internal fixation. Such supplemental internal fixation may include (but not be limited to) any appropriate screws, rods, staples, washers, cross connectors, and/or posterior hooks.

In another embodiment, Contraindications relating to use of the present invention may include (but not be limited to):
 Morbid obesity
 Mental illness
 Alcoholism and/or drug abuse
 Pregnancy
 Mental sensitivity/allergies
 Severe osteopenia
 Patients unwilling or unable to follow post-operative care instructions
 Certain circumstances not identified above as an Indication (e.g., as identified by any appropriate care giver)

In another embodiment, one or more of the components and/or the implant assembly may have a tapered lead-in (e.g., for easy insertion).

In another embodiment, each lateral spacer may be capable of supporting the vertebral column.

In another embodiment, the textured surface of the components and/or the implant assembly may allow for easy insertion and/or resistance to expulsion (see FIGS. 10-14 for additional textured surface examples (which examples are intended to be illustrative and not restrictive)).

Figure 15:
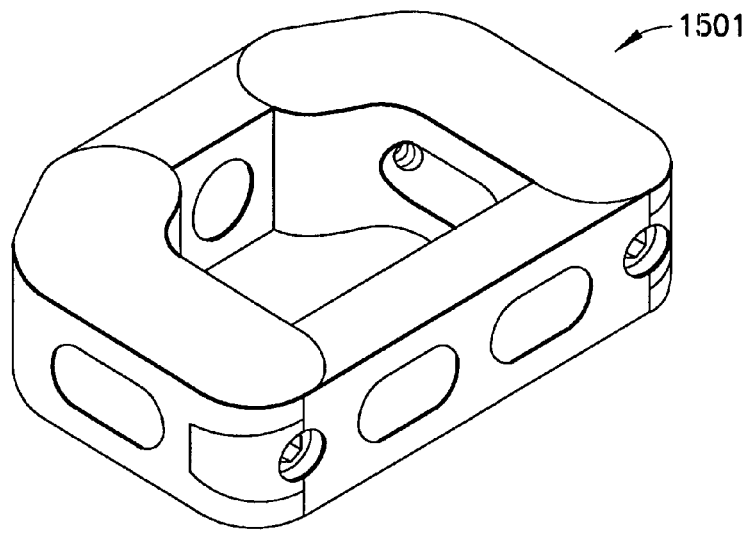
FIGS. 15 and 16 show, respectively, a perspective view and an exploded perspective view of another embodiment of the present invention.
Figure 16:
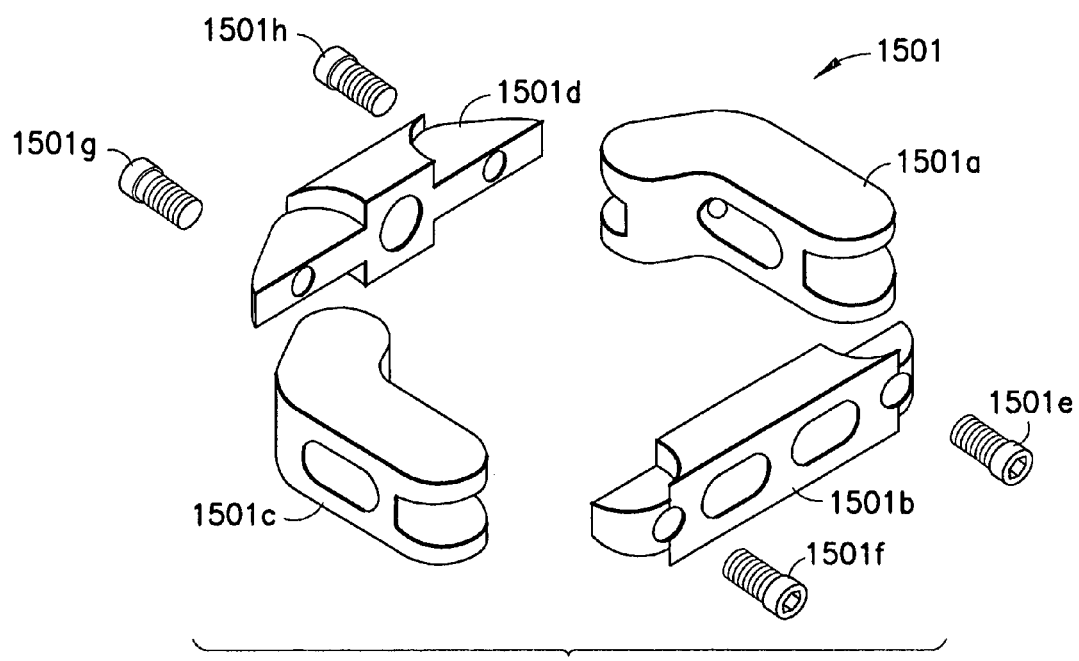
Figure 17A:
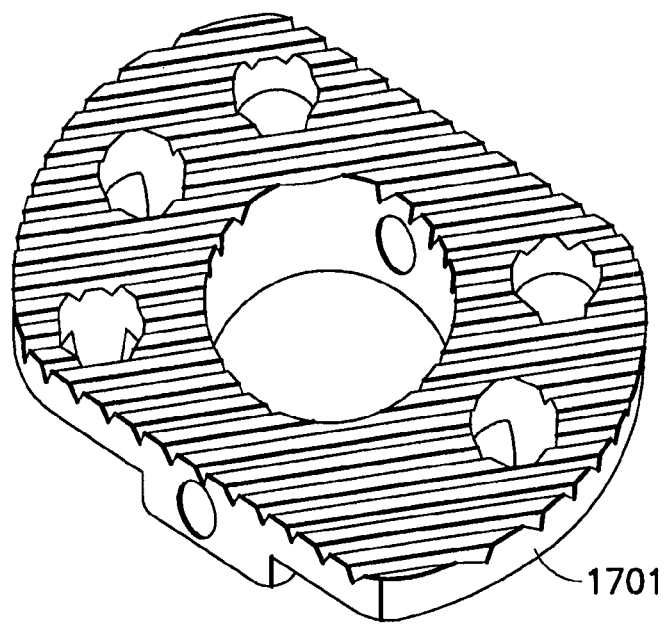
FIGS. 17A-17G show perspective views of various components according to an embodiment of the present invention.
Figure 17B:
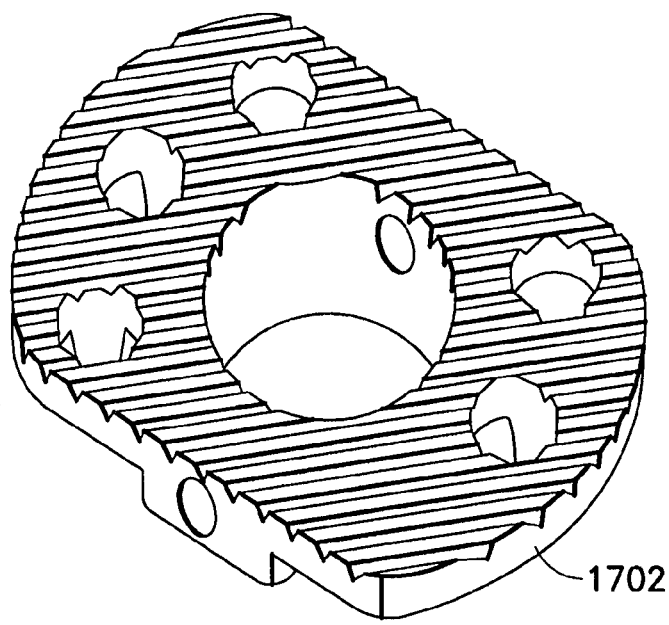
Figure 17C:
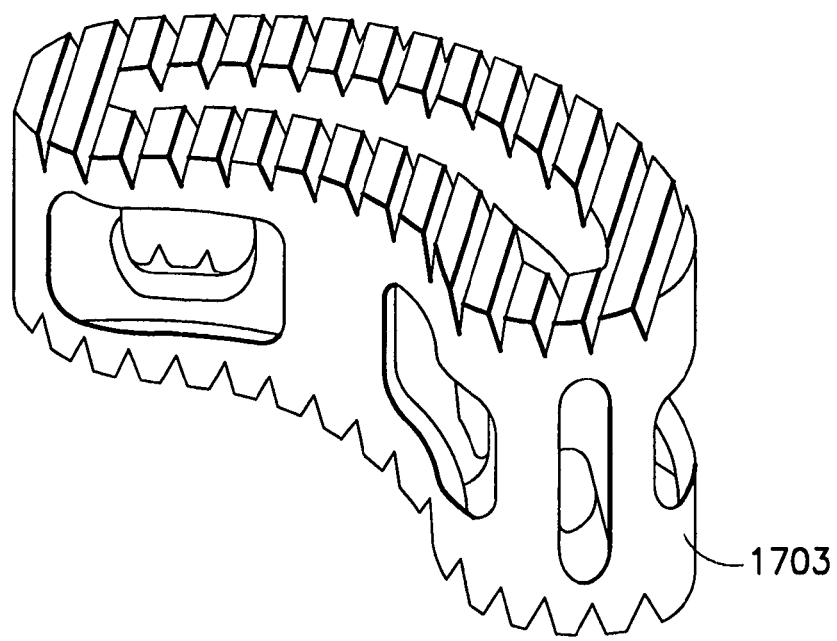
Figure 17D:
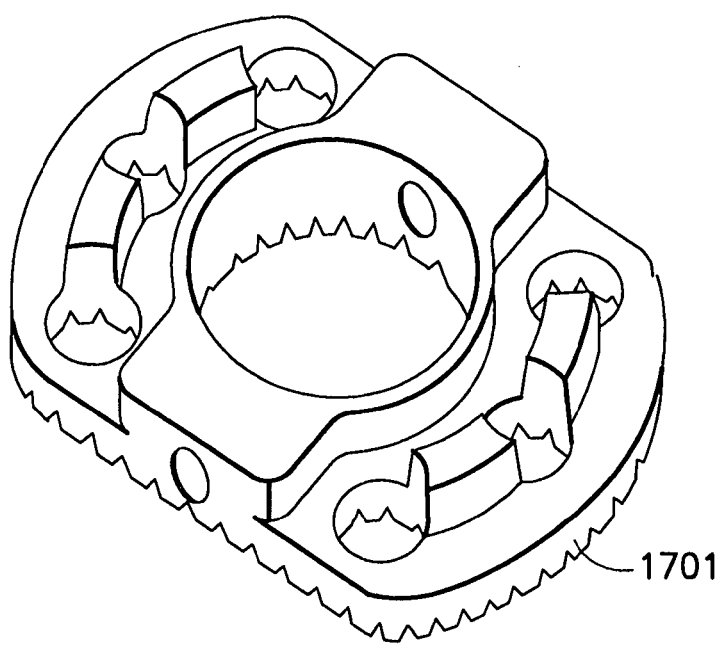
Figure 17E:
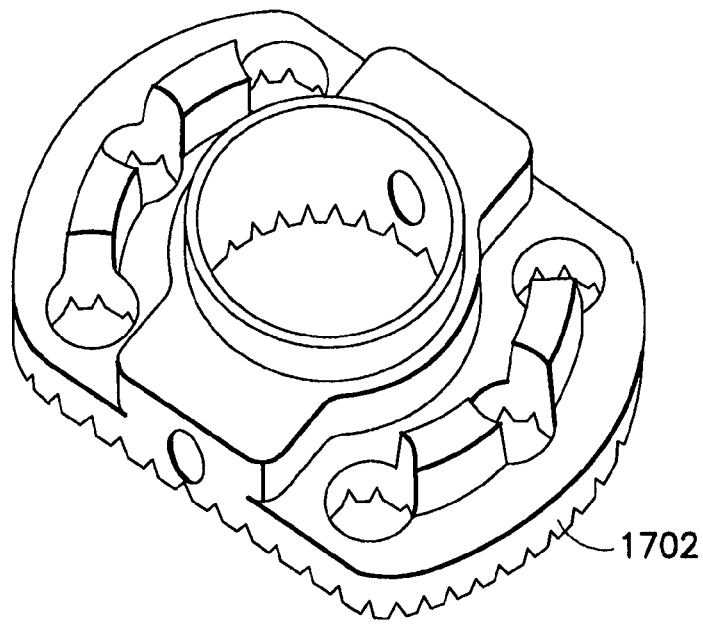
Figure 17F:
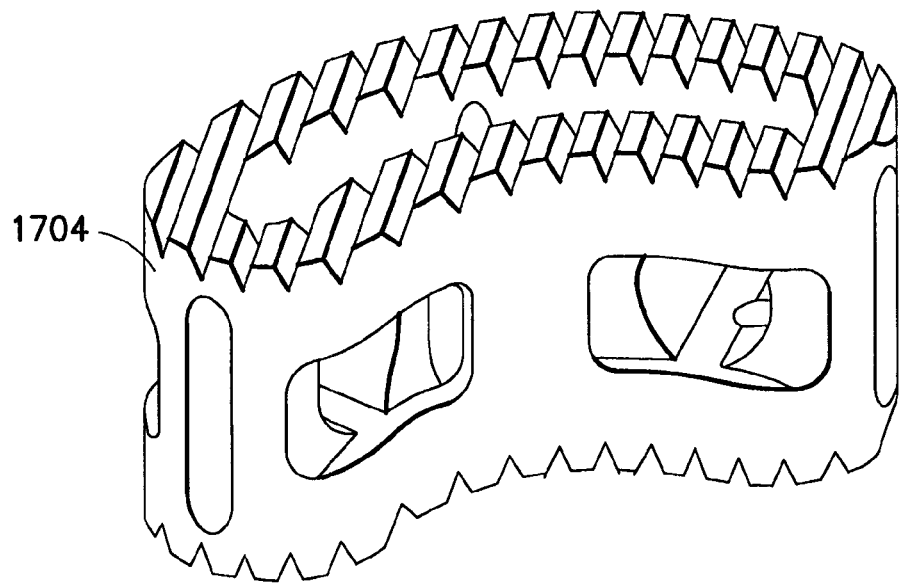
Figure 17G:
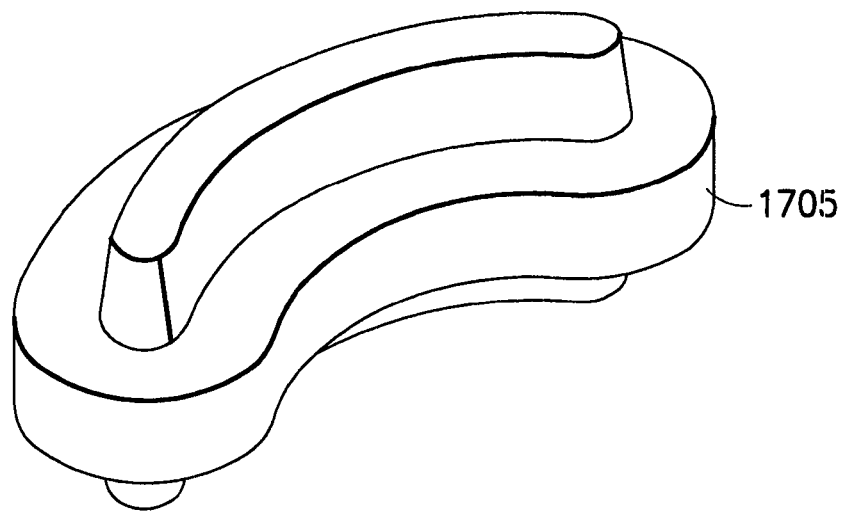
Figure 18:
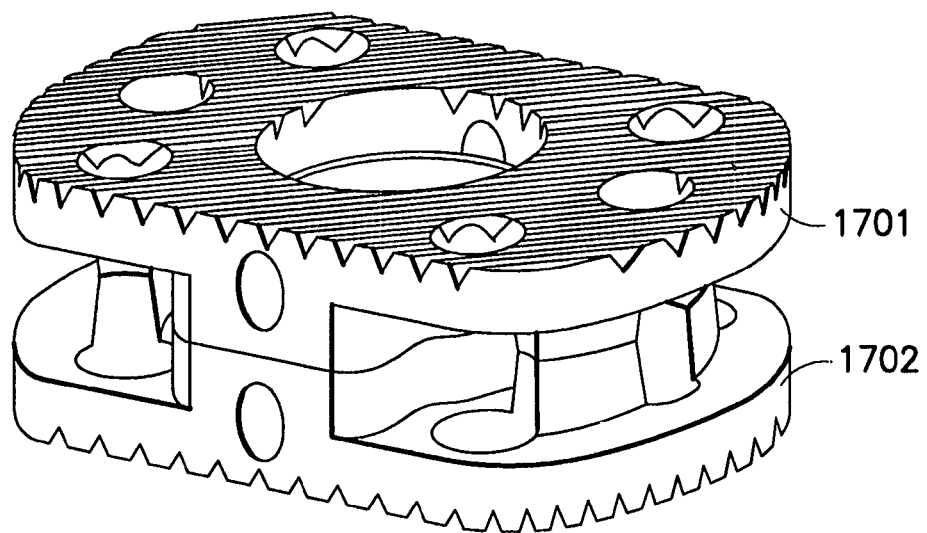
FIGS. 18, 19A, 19B, 20A, 20B and 21 show perspective views of various implant assemblies using the components of FIGS. 17A-17G.
Figure 19A:
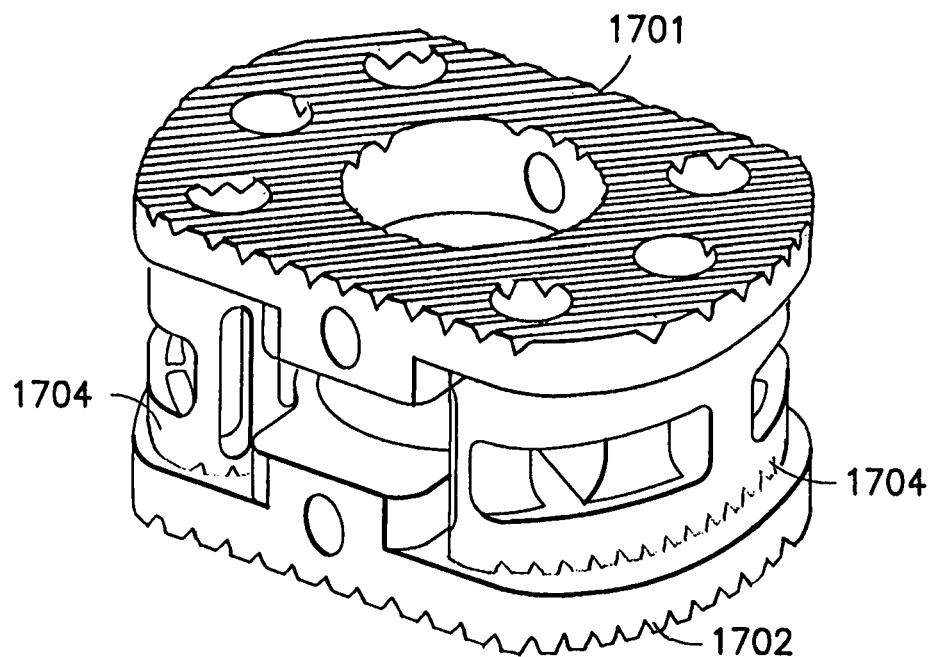
Figure 20A:
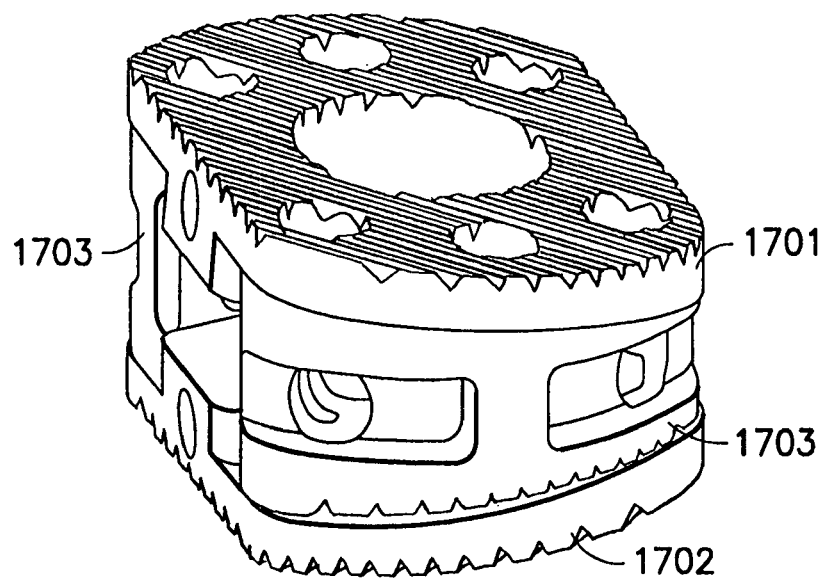
Figure 19B:
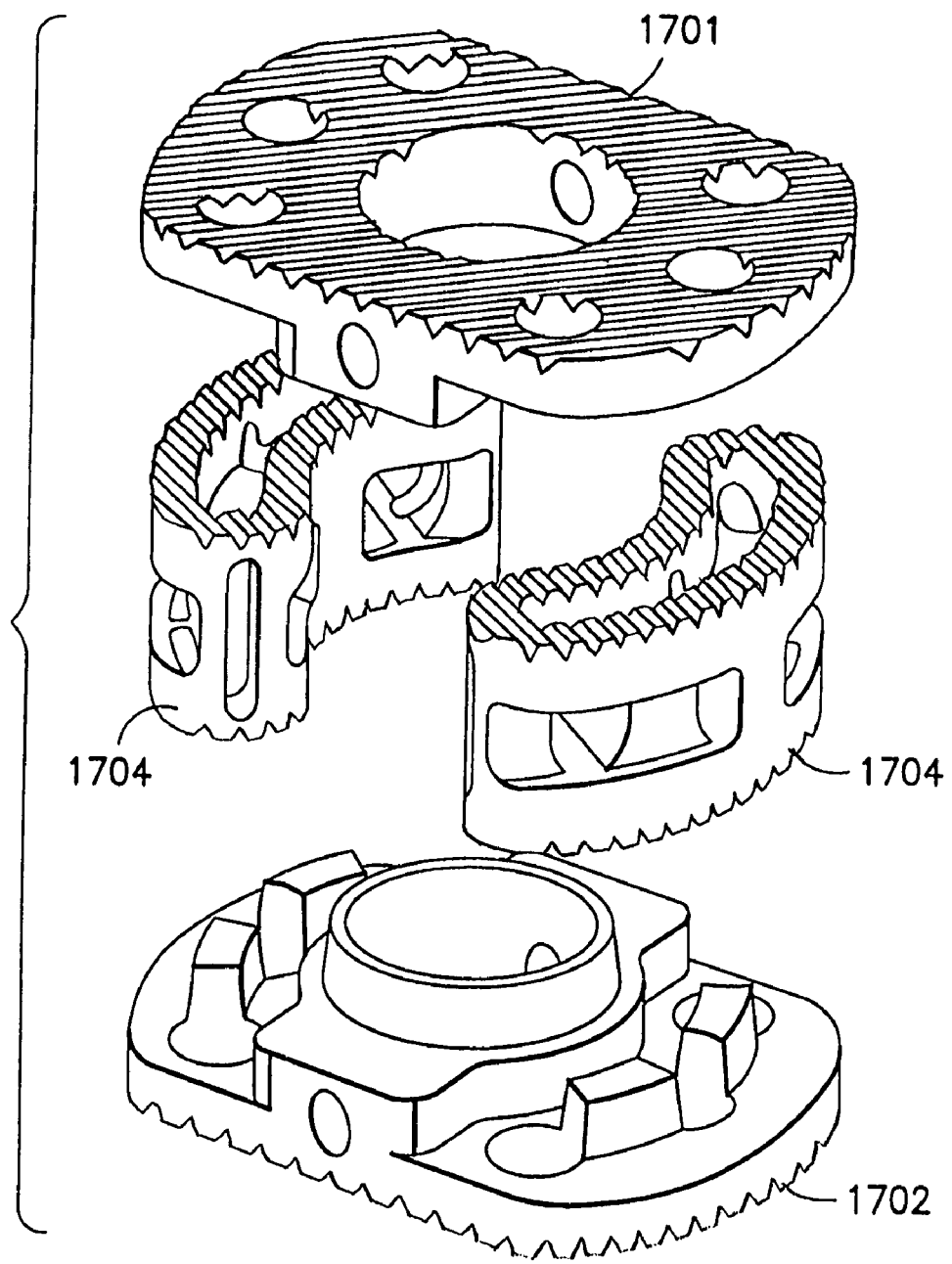
Figure 20B:
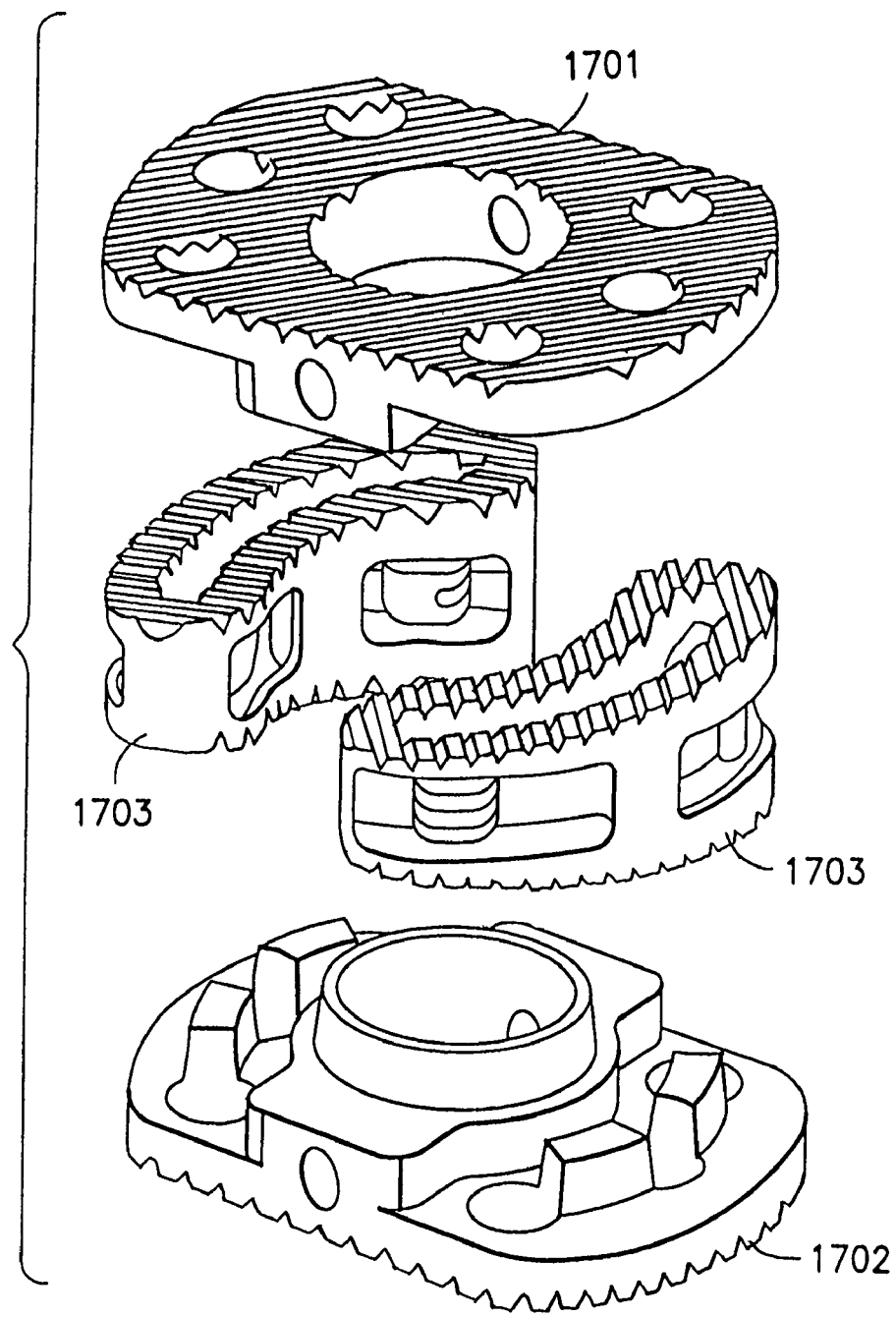
Figure 21:
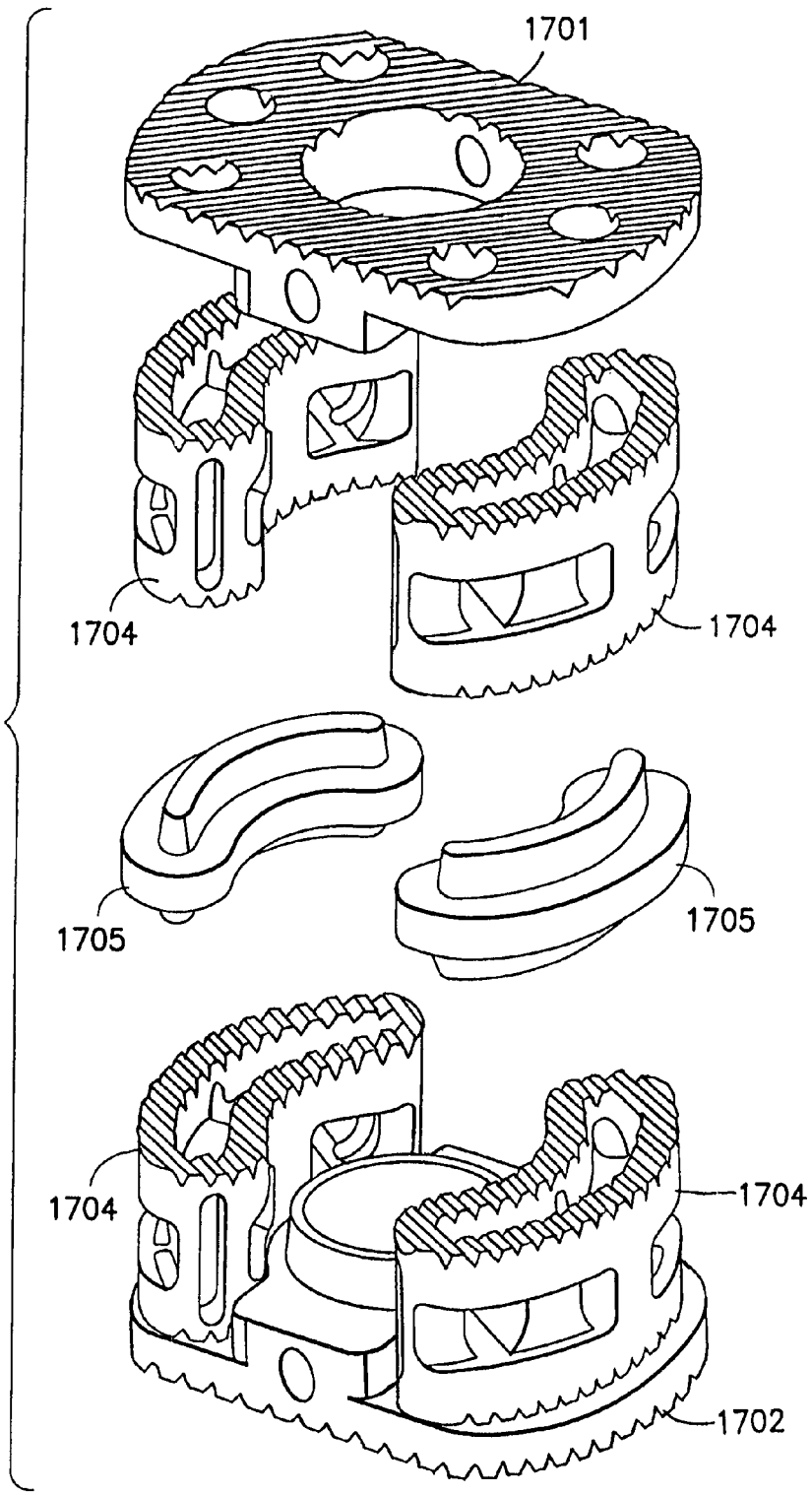
Figure 22A:
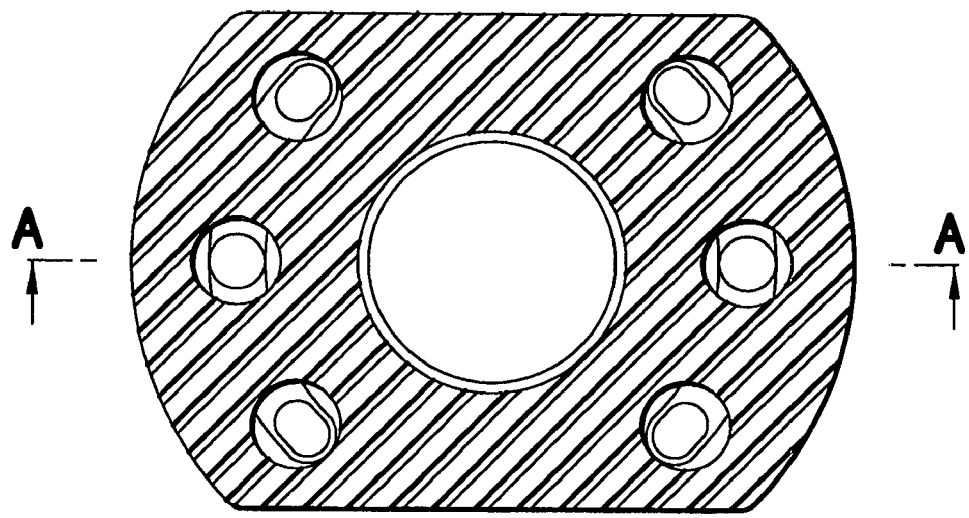
FIGS. 22A-22E show various views of an implant assembly using the components of FIGS. 17A-17G.
Figure 22B:
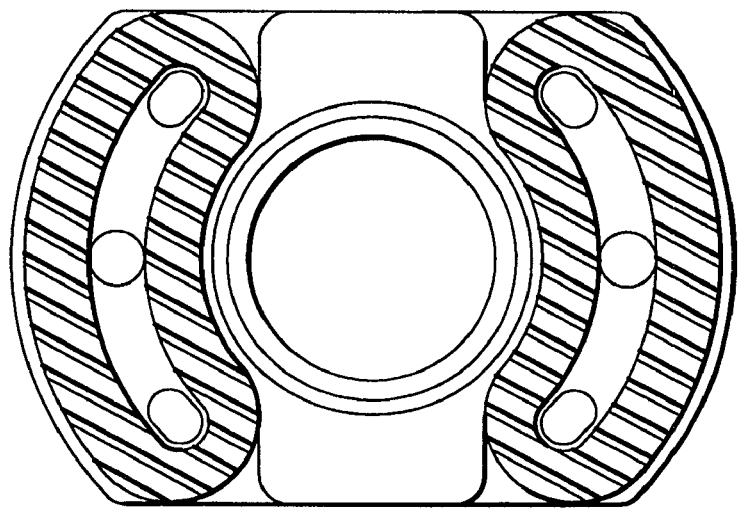
Figure 22C:
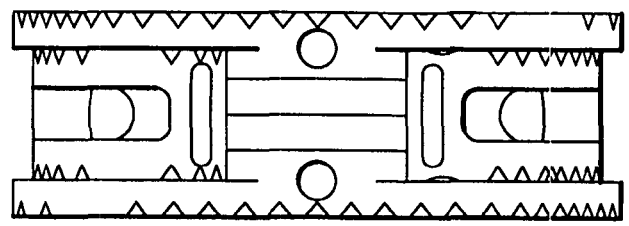
Figure 22D:
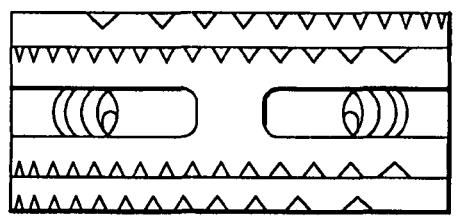
Figure 22E:
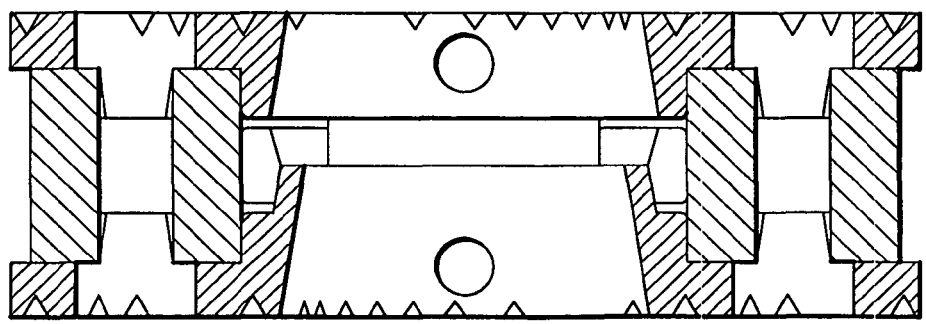

In another embodiment, multiple lateral spacer type components may be assembled in a "bridge" configuration (see FIGS. 15 and 16, for example).

In another embodiment, the components may be assembled as desired (see FIGS. 17A-17G, 18, 19A, 19B, 20A, 20B, 21 and 22A-22E, for example).

While a number of embodiments of the present invention have been described, it is understood that these embodiments are illustrative only, and not restrictive, and that many modifications may become apparent to those of ordinary skill in the art. For example, an implant assembly according to the present invention may be tested in accordance with ASTM F 2077-03 "Test Methods For Intervertebral Body Fusion Devices" (or a modified version thereof) and/or the FDA's Sep. 27, 2000 "Guidance for Spinal Systems 510(k)'s. Further, the lordotic angle may be any desired angle (e.g., 4°-8°). Further still, one or more components may be used separately from an implant assembly (e.g., one or more of the lateral spacers (non-lordotic and/or lordotic) may be implanted directly into the spine without use of a top and/or bottom endplate). Further still, the various components may take different shapes as desired and the various features may take on various specifics as desired (e.g., the various apertures may be of any desired number and/or shape). Further still, the apparatus (and/or its components) may, of course, have any desired dimensions (e.g., for any desired patient—man, woman or child). Further still, the apparatus (and/or its components) may be provided in a "line" or "family" of devices (e.g., small, medium and large; adult, child; male, female). Further still, the apparatus (and/or its components) may be provided in standard sizes. Further still, any desired locking mechanism(s) may be used to hold the various components together and/or in desired alignment. Further still, such locking may be capable of being unlocked (e.g., a mechanism and/or tool may be provided for unlocking the various components). Further still, lateral spacers(s) may be disposed adjacent one or more central spacers. Further still, any steps relating to manufacture and/or use may be performed in any desired order.

What is claimed is:

1. A vertebral body replacement apparatus for placement between a first vertebra and a second vertebra, comprising:
   a first endplate including a generally outward facing surface for contacting at least a portion of a lower face of the first vertebra and a generally inward facing surface including thereon at least two protrusions;
   a second endplate including a generally outward facing surface for contacting at least a portion of an upper face of the second vertebra and a generally inward facing surface including thereon at least two protrusions;
   a first lateral spacer including at least one aperture; and
   a second lateral spacer including at least one aperture;
   wherein, when the first and second lateral spacers are disposed between the first and second endplates such that the first endplate is above the first and second lateral spacers and the second endplate is below the first and second lateral spacers, the aperture of the first lateral spacer is configured to receive at least one of the protrusions of each of the first and second endplates and the aperture of the second lateral spacer is configured to receive at least one of the protrusions of each of the first and second endplates, wherein said first lateral spacer comprises PEEK and wherein said second lateral spacer comprises PEEK.

2. The apparatus of claim 1, wherein the mating of each of the protrusions with a respective one of the apertures provides lateral alignment between each of the first endplate, the second endplate, the first lateral spacer and the second lateral spacer.

3. The apparatus of claim 2, wherein at least one of the protrusions and at least one of a respective one of the apertures includes a locking mechanism for locking the protrusion in the aperture.

4. The apparatus of claim 3, wherein the locking mechanism of the protrusion and the locking mechanism of the aperture are configured to permit unlocking thereof.

5. The apparatus of claim 4, wherein the locking mechanism of the protrusion comprises a raised ridge and the locking mechanism of the aperture comprises an indentation.

6. The apparatus of claim 1, wherein the aperture of the first lateral spacer extends through the first lateral spacer and the aperture of the second lateral spacer extends through the second lateral spacer.

7. The apparatus of claim 1, wherein each of the first and second lateral spacers includes a respective upper aperture adjacent the generally inward facing surface of the first endplate for receiving at least one of the protrusions of the first endplate and each of the first and second lateral spacers includes a respective lower aperture adjacent the generally inward facing surface of the second endplate for receiving at least one of the protrusions of the second endplate.

8. The apparatus of claim 1, wherein the generally outward facing surface of the first endplate is textured and the generally outward facing surface of the second endplate is textured.

9. The apparatus of claim 8, wherein the texture is configured to aid in permitting bony ingrowth from the first and second vertebrae.

10. The apparatus of claim 8, wherein the texture is selected from the group including: (a) teeth; (b) grooves; and (c) ridges.

11. The apparatus of claim 1, wherein the first endplate, the second endplate, the first lateral spacer and the second lateral spacer are configured to define at least one hollow area when the first and second lateral spacers are disposed between the first and second endplates such that the first endplate is above the first and second lateral spacers and the second endplate is below the first and second lateral spacers.

12. The apparatus of claim 11, wherein the hollow area is configured to aid in permitting bony ingrowth from the first and second vertebrae.

13. A method of constructing a vertebral body replacement apparatus for placement between a first vertebra and a second vertebra, comprising:
   selecting a first endplate including a generally outward facing surface for contacting at least a portion of a lower face of the first vertebra and a generally inward facing surface including thereon at least two protrusions;
   selecting a second endplate including a generally outward facing surface for contacting at least a portion of an upper face of the second vertebra and a generally inward facing surface including thereon at least two protrusions;
   selecting a first lateral spacer including at least one aperture;
   selecting a second lateral spacer including at least one aperture; and
   placing the first and second lateral spacers between the first and second endplates such that the first endplate is above the first and second lateral spacers and the second endplate is below the first and second lateral spacers and such that the aperture of the first lateral spacer receives at least one of the protrusions of each of the first and second endplates and the aperture of the second lateral spacer receives at least one of the protrusions of each of the first and second endplates, wherein said first lateral spacer comprises PEEK and wherein said second lateral spacer comprises PEEK.

14. The method of claim 13, wherein the mating of each of the protrusions with a respective one of the apertures provides lateral alignment between each of the first endplate, the second endplate, the first lateral spacer and the second lateral spacer.

15. The method of claim 14, wherein at least one of the protrusions and at least one of a respective one of the apertures includes a locking mechanism for locking the protrusion in the aperture.

16. The method of claim 15, wherein the locking mechanism of the protrusion and the locking mechanism of the aperture are configured to permit unlocking thereof.

17. The method of claim 13, wherein the aperture of the first lateral spacer extends through the first lateral spacer and the aperture of the second lateral spacer extends through the second lateral spacer.

18. The method of claim 13, wherein each of the first and second lateral spacers includes a respective upper aperture adjacent the generally inward facing surface of the first endplate for receiving at least one of the protrusions of the first endplate and each of the first and second lateral spacers includes a respective lower aperture adjacent the generally inward facing surface of the second endplate for receiving at least one of the protrusions of the second endplate.

19. The method of claim 13, wherein the steps are carried out by:
   first, selecting the first endplate;
   second, selecting the second endplate;
   third, selecting the first lateral spacer;
   fourth, selecting the second lateral spacer; and
   fifth, placing the first and second lateral spacers between the first and second endplates.

20. A method of stabilizing a spine, comprising:
   selecting, for a vertebral body replacement apparatus, a first endplate including a generally outward facing surface for contacting at least a portion of a lower face of a first vertebra and a generally inward facing surface including thereon at least two protrusions;
   selecting, for the vertebral body replacement apparatus, a second endplate including a generally outward facing surface for contacting at least a portion of an upper face of a second vertebra and a generally inward facing surface including thereon at least two protrusions;
   selecting, for the vertebral body replacement apparatus, a first lateral spacer including at least one aperture;
   selecting, for the vertebral body replacement apparatus, a second lateral spacer including at least one aperture;
   constructing the vertebral body replacement apparatus by placing the first and second lateral spacers between the first and second endplates such that the first endplate is above the first and second lateral spacers and the second endplate is below the first and second lateral spacers and such that the aperture of the first lateral spacer receives at least one of the protrusions of each of the first and second endplates and the aperture of the second lateral spacer receives at least one of the protrusions of each of the first and second endplates, wherein said first lateral spacer comprises PEEK and wherein said second lateral spacer comprises PEEK; and placing the vertebral body replacement apparatus between the first and second vertebrae.

21. The method of claim 20, wherein the vertebral body replacement apparatus is configured to be placed in one of the thoracic and lumbar spinal regions.

22. The method of claim 20, wherein the steps are carried out by:
   first, selecting the first endplate;
   second, selecting the second endplate;
   third, selecting the first lateral spacer;
   fourth, selecting the second lateral spacer;
   fifth, constructing the vertebral body replacement apparatus; and
   sixth, placing the vertebral body replacement apparatus between the first and second vertebrae.

* * * * *